United States Patent
Racenet et al.

(10) Patent No.: US 9,931,116 B2
(45) Date of Patent: Apr. 3, 2018

(54) BUTTRESS COMPOSITION

(71) Applicant: Covidien LP, Mansfield, MA (US)

(72) Inventors: Danyel Racenet, Killingworth, CT (US); Steven L. Bennett, Cheshire, CT (US); Erik Carlson, Meriden, CT (US); Kenneth H. Whitfield, North Haven, CT (US); Gregg Krehel, Newtown, CT (US)

(73) Assignee: COVIDIEN LP, Mansfield, MA (US)

( * ) Notice: Subject to any disclaimer, the term of this patent is extended or adjusted under 35 U.S.C. 154(b) by 418 days.

(21) Appl. No.: 13/748,684

(22) Filed: Jan. 24, 2013

(65) Prior Publication Data

US 2013/0209659 A1 Aug. 15, 2013

Related U.S. Application Data

(60) Provisional application No. 61/597,321, filed on Feb. 10, 2012.

(51) Int. Cl.
*A61B 17/064* (2006.01)
*A61L 31/14* (2006.01)
*A61B 17/072* (2006.01)

(52) U.S. Cl.
CPC .... *A61B 17/0644* (2013.01); *A61B 17/07292* (2013.01); *A61L 31/145* (2013.01)

(58) Field of Classification Search
USPC ................. 424/424; 623/1.15; 227/176.1
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |

(Continued)

FOREIGN PATENT DOCUMENTS

| | | |
|---|---|---|
| CA | 2 667 434 | 5/2008 |
| DE | 1 99 24 311 A1 | 11/2000 |

(Continued)

OTHER PUBLICATIONS

Anonymous, Bovine Serum Albumin, 2014, Wikipedia, http://en.wikipedia.org/wiki/Bovine_Serum_Albumin.*

(Continued)

*Primary Examiner* — Dah-Wei D Yuan
*Assistant Examiner* — Andrew Bowman

(57) ABSTRACT

A tissue buttress is provided on at least a first and second jaw of a surgical stapling apparatus. The tissue buttress comprises an electrophilic component and a nucleophilic component. At least a portion of the tissue buttress may be disposed within either or both of the staple pockets and staple forming pockets, securing the tissue buttress to at least one of the staple jaws.

20 Claims, 10 Drawing Sheets

(56) References Cited

U.S. PATENT DOCUMENTS

| | | |
|---|---|---|
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,592,597 B2 | 7/2003 | Grant et al. |
| 6,605,294 B2 | 8/2003 | Sawhney |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,241,300 B2 | 2/2007 | Sharkawy et al. |
| 7,239,449 B2 | 6/2007 | Sharkawy et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |

(56) References Cited

U.S. PATENT DOCUMENTS

| | | |
|---|---|---|
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1* | 10/2007 | Gertner ............... 424/424 |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0220047 A1 | 9/2008 | Sawhney et al. |
| 2008/0230583 A1* | 9/2008 | Heinrich ............ 227/176.1 |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0149942 A1* | 6/2009 | Edelman et al. ............ 623/1.15 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |

(56) References Cited

U.S. PATENT DOCUMENTS

| | | |
|---|---|---|
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0010170 A1 | 1/2011 | Burns et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0036895 A1 | 2/2011 | Marczyk et al. |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

FOREIGN PATENT DOCUMENTS

| | | |
|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 | 8/2009 |
| EP | 2 090 252 | 8/2009 |
| EP | 2 198 787 A1 | 6/2010 |
| EP | 2 236 098 A2 | 10/2010 |
| EP | 2 236 099 | 10/2010 |
| EP | 2292276 A2 | 3/2011 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 2007-124166 | 5/2007 |
| WO | WO 90/05489 A1 | 5/1990 |
| WO | WO 95/16221 A1 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

Extended European Search Report corresponding to EP 12 19 1035.0, dated Jan. 11, 2013 and dated Jan. 18, 2013; 7 pages.

Extended European Search Report corresponding to EP 12 19 6904.2, dated Mar. 28, 2013 and dated Jul. 26, 2013; 8 pages.

Extended European Search Report corresponding to EP 12 19 8749.9, dated May 21, 2013 and dated May 31, 2013; 8 pages.

(56) References Cited

OTHER PUBLICATIONS

Extended European Search Report corresponding to EP 07 00 5842.5, dated May 13, 2013 and dated May 29, 2013; 7 pages.
Extended European Search Report corresponding to EP 12 19 8776.2, dated May 16, 2013 and dated May 27, 2013; 8 pages.
Extended European Search Report corresponding to EP 13 15 6297.7, dated Jun. 4, 2013 and dated Jun. 13, 2013; 7 pages.
Extended European Search Report corresponding to EP 13 17 3985.6, dated Aug. 19, 2013 and dated Aug. 28, 2013; 6 pages.
Extended European Search Report corresponding to EP 13 17 3986.4, dated Aug. 20, 2013 and dated Aug. 29, 2013; 7 pages.
European Search Report corresponding to EP 05 02 2585.3, dated Jan. 25, 2006 and dated Feb. 3, 2006; 4 pages.
European Search Report corresponding to EP 06 00 4598, dated Jun. 22, 2006; 2 pages.
European Search Report corresponding to EP 06 01 6962.0, dated Jan. 3, 2007 and dated Jan. 11, 2007; 10 pages.
International Search Report corresponding to International Application No. PCT/US2005/036740, dated Feb. 20, 2007 and dated Mar. 23, 2007; 8 pages.
International Search Report corresponding to International Application No. PCT/US2007/022713, dated Apr. 21, 2008 and dated May 15, 2008; 1 page.
International Search Report corresponding to International Application No. PCT/US2008/002981, dated Jun. 9, 2008 and dated Jun. 26, 2008; 2 pages.
European Search Report corresponding to EP 08 25 1779, dated Jul. 14, 2008 and dated Jul. 23, 2008; 5 pages.
European Search Report corresponding to EP 08 25 1989.3, dated Mar. 11, 2010 and dated Mar. 24, 2010; 6 pages.
European Search Report corresponding to EP 10 25 0639.1, dated Jun. 17, 2010 and dated Jun. 28, 2010; 7 pages.
European Search Report corresponding to EP 10 25 0715.9, dated Jun. 30, 2010 and dated Jul. 20, 2010; 3 pages.
European Search Report corresponding to EP 05 80 4382.9, dated Oct. 5, 2010 and dated Oct. 12, 2010; 3 pages.
European Search Report corresponding to EP 10 25 1437.9, dated Nov. 22, 2010 and dated Dec. 16, 2010; 3 pages.
European Search Report corresponding to EP 09 25 2897.5, dated Feb. 7, 2011 and dated Feb. 15, 2011; 3 pages.
European Search Report corresponding to EP 10 25 0642.5, dated Mar. 25, 2011 and dated Apr. 4, 2011; 4 pages.
European Search Report corresponding to EP 11 18 8309.6, dated Dec. 15, 2011 and dated Jan. 12, 2012; 3 pages.
European Search Report corresponding to EP 12 15 2229.6, dated Feb. 23, 2012 and dated Mar. 1, 2012; 4 pages.
European Search Report corresponding to EP 12 15 0511.9, dated Apr. 16, 2012 and dated Apr. 24, 2012; 7 pages.
European Search Report corresponding to EP 12 15 2541.4, dated Apr. 23, 2012 and dated May 3, 2012; 10 pages.
European Search Report corresponding to EP 12 16 5609.4, dated Jul. 5, 2012 and dated Jul. 13, 2012; 8 pages.
European Search Report corresponding to EP 12 15 8861.0, dated Jul. 17, 2012 and dated Jul. 24, 2012; 9 pages.
European Search Report corresponding to EP 12 16 5878.5, dated Jul. 24, 2012 and dated Aug. 6, 2012; 8 pages.
Extended European Search Report corresponding to EP 12 18 6175.1, dated Jan. 15, 2013 and dated Jan. 23, 2013; 7 pages.
Extended European Search Report corresponding to EP 12 19 1114.3, dated Jan. 23, 2013 and dated Jan. 31, 2013; 10 pages.
Extended European Search Report corresponding to EP 12 19 2224.9, dated Mar. 14, 2013 and dated Mar. 26, 2013; 8 pages.
Extended European Search Report corresponding to EP 12 19 6911.7, dated Apr. 18, 2013 and dated Apr. 24, 2013; 8 pages.
Extended European Search Report corresponding to EP 08 72 6500.5, dated Feb. 20, 2014 and dated Mar. 3, 2014; (7 pp).
Extended European Search Report corresponding to EP 13 19 5919.9, dated Feb. 10, 2014 and dated Mar. 3, 2014; (7 pp).
Extended European Search Report corresponding to EP 13 19 2123.1, dated Jan. 30, 2014 and dated Feb. 10, 2014; (8 pp).
Extended European Search Report corresponding to EP 13 19 6816.6, dated Mar. 28, 2014 and dated Apr. 9, 2014; (9 pp).
Extended European Search Report corresponding to EP 13 19 4995.0, dated Jun. 5, 2014 and dated Jun. 16, 2014; (5 pp).
Extended European Search Report corresponding to EP 13 19 5019.8, dated Mar. 14, 2014 and dated Mar. 24, 2014; (7 pp).
Extended European Search Report corresponding to EP 13 19 2111.6, dated Feb. 13, 2014 and dated Feb. 27, 2014; (10 pp).
Extended European Search Report corresponding to EP 13 19 7958.5, dated Apr. 4, 2014 and dated Apr. 15, 2014; (8 pp).
Extended European Search Report corresponding to EP 14 15 6342.9, dated Jul. 22, 2014 and dated Jul. 29, 2014; (8 pp).
Extended European Search Report corresponding to EP 14 15 7195.0, dated Jun. 5, 2014 and dated Jun. 18, 2014; (9 pp).
Extended European Search Report from Application No. 13154571.7 dated Oct. 20, 2014.
Extended European Search Report corresponding to EP 14 16 9739.1, dated Aug. 19, 2014 and Aug. 29, 2014; (7 pp).
Extended European Search Report corresponding to EP 14 15 7997.9, dated Sep. 9, 2014 and dated Sep. 17, 2014; (8 pp).
Extended European Search Report corresponding to EP 14 16 8904.2, dated Sep. 10, 2014 and dated Sep. 18, 2014; (8 pp).
Extended European Search Report corresponding to EP 13 19 4995.0, dated Jun. 5, 2014 and dated Oct. 13, 2014; (10 pp).
Extended European Search Report corresponding to EP 14 18 1125.7, dated Oct. 16, 2014 and dated Oct. 24, 2014; (7 pp).
Extended European Search Report corresponding to EP 14 18 1127.3, dated Oct. 16, 2014 and dated Nov. 10, 2014; (8 pp).
Extended European Search Report corresponding to EP 14 19 0419.3, dated Mar. 24, 2015 and dated Mar. 30, 2015; (6 pp).
Extended European Search Report corresponding to EP 13 17 7437.4, dated Sep. 11, 2013 and dated Sep. 19, 2013; (6 pp).
Extended European Search Report corresponding to EP 13 17 7441.6, dated Sep. 11, 2013 and dated Sep. 19, 2013; (6 pp).
Extended European Search Report corresponding to EP 07 86 1534.1, dated Sep. 20, 2013 and mailed Sep. 30, 2013; (5 pp).
Extended European Search Report corresponding to EP 13 18 3876.5, dated Oct. 14, 2013 and dated Oct. 24, 2013; (5 pp).
Extended European Search Report corresponding to EP 13 17 1856.1, dated Oct. 29, 2013 and dated Nov. 7, 2013; (8 pp).
Extended European Search Report corresponding to EP 13 18 0373.6, dated Oct. 31, 2013 and dated Nov. 13, 2013; (7 pp).
Extended European Search Report corresponding to EP 13 18 0881.8, dated Nov. 5, 2013 and dated Nov. 14, 2013; (6 pp).
Extended European Search Report corresponding to EP 13 17 6895.4, dated Nov. 29, 2013 and dated Dec. 12, 2013; (5 pp).
Extended European Search Report corresponding to EP 13 18 2911.1, dated Dec. 2, 2013 and dated Dec. 16, 2013; (8 pp).
Extended European Search Report corresponding to EP 10 25 1795.0, dated Dec. 11, 2013 and dated Dec. 20; 2013; (6 pp).
Extended European Search Report corresponding to EP 13 18 7911.6, dated Jan. 22, 2014 and dated Jan. 31, 2014; (8 pp).

* cited by examiner

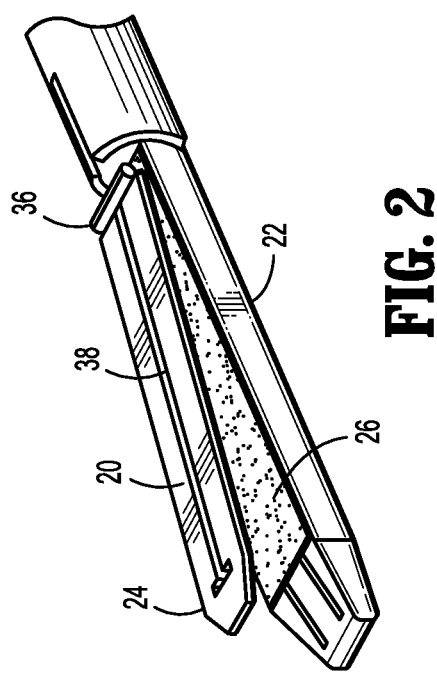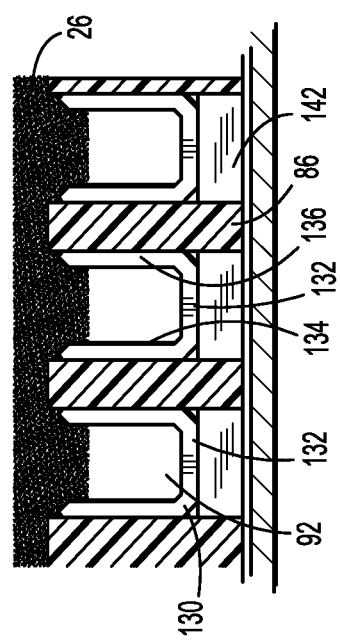

BUTTRESS COMPOSITION

CROSS-REFERENCE TO RELATED APPLICATION

The present application claims the benefit of and priority to U.S. Provisional Application Ser. No. 61/597,321, filed on Feb. 10, 2012, the entire disclosure of which is incorporated by reference herein.

BACKGROUND

Technical Field

The present disclosure relates to buttress materials used in joining body tissue and methods for attaching buttress materials to surgical instruments. More particularly, the present disclosure relates to compositions of staple line buttress materials which include biocompatible crosslinked polymers having electrophilic and nucleophilic functional groups.

Background of Related Art

Surgical stapling devices are employed by surgeons to sequentially or simultaneously apply one or more rows of fasteners, e.g., staples or two-part fasteners, to body tissue for the purpose of joining segments of body tissue together. Such devices generally consist of a pair of jaws comprising a staple anvil and cartridge between which the body tissue to be joined is placed. When the stapling device is actuated, or "fired", a firing member or members contact staple drive members in one of the jaws. The staple drive members push the surgical staples through the body tissue and into an anvil in an opposite jaw which crimps the staples closed. If tissue is to be removed or separated, a knife blade can be provided in the jaws of the device to cut the tissue between the lines of staples.

When stapling relatively thin, diseased, or fragile tissues, a buttress may be employed to seal the staple line against air or fluid leakage. Additionally, a buttress may be used to reinforce the staple line against the tissue to prevent tears in the tissue or pulling of the staples through the tissue. A layer of buttress material is placed against the tissue and the tissue is stapled in conventional manner. The buttress provides support and reinforcement to the tissue and staple line.

Biocompatible polymers for use as tissue reinforcements, such as buttresses, remain desirable. Polymers having parameters which can be easily adjusted to accommodate specific procedures remain desired. Further, it would also be advantageous to provide a buttress which can accommodate various sizes and shapes of surgical instrument loading units (e.g., circular, linear, etc), providing ease of manufacturing.

SUMMARY

The present disclosure relates to a medical device comprising a jaw assembly including a first jaw and a second jaw, at least one of the first jaw and the second jaw defining staple pockets for retaining staples and a buttress disposed on at least one of the first jaw and the second jaw; the buttress comprising an electrophilic component and a nucleophilic component. In particular, the electrophilic component may comprise N-hydroxysuccinimide and the nucleophilic component may comprise a natural component. The natural component may comprise albumin, having a molecular weight of from about 60,000 g/mol to about 70,000 g/mol.

In certain embodiments, the electrophilic component may further comprise polyethylene glycol. Further, the electrophilic component may have multiple arms, such as four, eight, or ten arms.

Buttresses of the present disclosure may comprise a porous material and in some embodiments, may be lyophilized. In certain examples, the buttress may be absorbent, bioabsorbable or may provide hemostasis in situ.

In embodiments, at least a portion of the buttress may be at least partially disposed within at least one staple pocket or one staple forming bucket.

Method for making a tissue buttress are also disclosed herein including applying a hydrogel to at least one of a first jaw and a second jaw of a surgical stapler; and lyophilizing the hydrogel disposed on at least one of the first jaw and the second jaw of the surgical stapler.

An alternate method for making a tissue buttress are also disclosed herein including the steps of applying a polymer composition to at least one of a staple anvil and a staple cartridge; crosslinking the polymer composition disposed on at least one of the staple anvil and staple cartridge; and, lyophilizing the polymer composition to create a tissue buttress.

DESCRIPTION OF THE DRAWINGS

Various embodiments of the presently disclosed systems for attaching staple line buttress materials to a surgical stapling instrument are disclosed herein with reference to the drawings, wherein:

FIG. 2 is a perspective view of the distal end of the surgical stapling instrument of FIG. 1;

FIG. 3 is a cross-sectional view of the cartridge of FIG. 1:

DETAILED DESCRIPTION OF EMBODIMENTS

Figure 1:
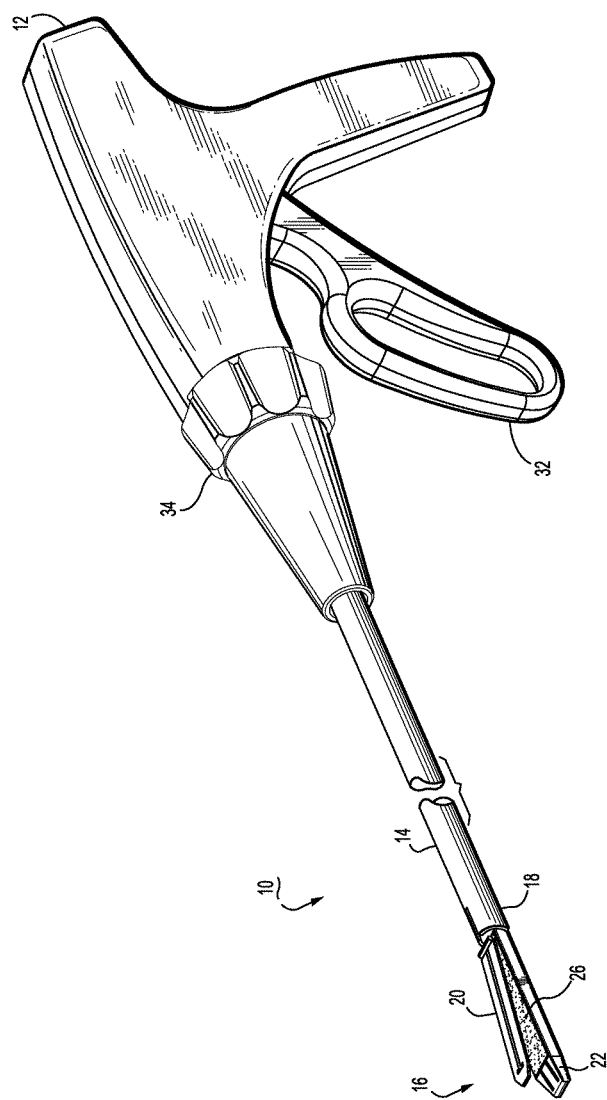
FIG. 1 is a perspective view of a surgical stapling instrument incorporating a buttress of the present disclosure.

The present disclosure provides tissue reinforcements and methods for attaching tissue reinforcements to surgical instruments to provide tissue support. Tissue reinforcements referred to herein include, but are not limited to, buttresses, pledgets and scaffolds which are attached to or used in combination with surgical instruments such as surgical staplers or sutures.

The buttress may be preformed or provided on the surgical instrument for supporting tissue closure and providing hemostasis to the wound. In embodiments, the buttress may deliver and/or release biological factors/molecules and/or cells at the site of the wound. For example, the buttress may assist in providing additional wound clotting factors, and/or assist in native tissue regrowth by providing surrounding tissue with needed nutrients and bioactive agents. In embodiments, the tissue buttress may be biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Buttresses of the present disclosure include an electrophilic component, sometimes referred to herein as an electrophilic crosslinker, and a nucleophilic component. The nucleophilic component may be crosslinked by the electrophilic crosslinker, and subsequently lyophilized to form the tissue buttress. In particular, the nucleophilic component may be a natural or synthetic component which may be released at the site of the wound as the buttress degrades. The term "natural component" as used herein includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic/recombinant materials, as well as methods capable of producing materials with the same structure and components as natural materials.

The buttress comprises at least one component having functional groups which are electrophilic or nucleophilic. The terms "nucleophile" and "nucleophilic" refer to a functional group that is electron rich, has an unshared pair of electrons acting as a reactive site, and reacts with a positively charged or electron-deficient site, generally present on another molecule. The terms "electrophile" and "electrophilic" refer to a functional group that is susceptible to nucleophilic attack, i.e., susceptible to reaction with an incoming nucleophilic group. Electrophilic groups herein are positively charged or electron-deficient typically electron-deficient. More specifically, electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first component may react with a second set of nucleophilic functional groups on a second component. When the components are mixed in an environment that permits reaction (e.g., as relating to pH or solvent), the functional groups react with each other to form covalent bonds (crosslinked polymer). The term "functional group" as used herein refers to electrophilic or nucleophilic groups capable of reacting with each other to form a bond.

Electrophilic functional groups include for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In particular embodiments, the electrophilic functional group comprises NHS.

The electrophilic and nucleophilic components may further have biologically inert and water soluble cores, as well as non-water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); polysaccharides, such as dextran, chitosan, alginates, carboxymethylcellulose, oxidized cellulose, hydroxyethylcellulose, hydroxymethylcellulose; hyaluronic acid; and proteins such as albumin, collagen, casein, and gelatin. Combinations of the foregoing polymers may be utilized. In particular, polyethers, and more particularly poly(oxyalkylenes) or poly(ethylene glycol) or polyethylene glycol, may be utilized in some embodiments. When the core is small in molecular nature, any of a variety of hydrophilic functionalities can be used to make the first and second components water soluble. For example, functional groups like hydroxyl, amine, sulfonate and carboxylate, which are water soluble, may be used to make the precursor water soluble. For example, the N-hydroxysuccinimide ester of subaric acid is insoluble in water, but by adding a sulfonate group to the succinimide ring, the NHS ester of subaric acid may be made water soluble, without affecting its reactivity towards amine groups.

Each of the first and second components may be multifunctional, meaning that it may include two or more electrophilic or nucleophilic functional groups, such that, for example, a nucleophilic functional group on the first component may react with an electrophilic functional group on the second component to form a covalent bond. At least one of the first or second components includes more than two functional groups, so that, as a result of electrophilic-nucleophilic reactions, the components combine to form cross-linked polymeric products, e.g., a buttress. It should be noted that the components described herein may be, e.g., a monomer, a macromer, or a polymer.

The electrophilic component may be multi-armed, for example, a multi-armed PEG having greater than three arms. In certain embodiments, the electrophilic component comprises four PEG arms extending from a core. Alternatively, six, eight, or more arms can extend from a core. The core may be the same or different from the macromolecule forming the arms. For example, the core may be PEG and the multiple arms may also be PEG.

The molecular weight (MW) of the electrophilic crosslinker may be from about 1,000 grams/mol (g/mol) to about 100,000 g/mol; in embodiments from about 2,000 g/mol to about 40,000 g/mol. Multi-arm precursors may have a molecular weight that varies depending on the number of arms. For example, an arm having a 1000 MW of PEG has enough $CH_2CH_2O$ groups to total at least 1000 MW. The combined molecular weight of an individual arm may be from about 250 g/mol to about 5,000 g/mol; in embodiments from about 1,000 g/mol to about 3,000 g/mol; in embodiments from about 1,250 g/mol to about 2,500 g/mol. In embodiments, the electrophilic crosslinker may be a multi-arm PEG functionalized with multiple NHS groups having, for example, four, six or eight arms and a molecular weight from about 5,000 g/mol to about 25,000 g/mol. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

The electrophilic component provides an electrophilic functional group capable of bonding with nucleophiles on the nucleophilic component, which, in embodiments, comprises albumin. In particular, the nucleophilic groups found on albumin include, for example, $—NH_2$. In certain embodiments, the albumin comprises bovine serum albumin (BSA), having a MW of about 66,000 g/mol and containing 60 lysine residues. Albumin is commercially available from, for example, SeraCare. Albumin includes multiple amine groups and is the most prevalent protein in the body. Albumin may provide cellular building blocks or cellular nutrients to the tissue. Further, albumin may aid in the tissue hemostasis.

In certain embodiments, the nucleophilic component may comprise natural component such as, for example, collagen, gelatin, blood (including serum, which may be whole serum or extracts therefrom), hyaluronic acid, other serum proteins, serum concentrates, platelet rich plasma (prp), combinations thereof, and the like. Additional suitable natural components which may be utilized or added to another natural component, sometimes referred to herein as a bioactive agent, include, for example, stem cells, DNA, RNA, enzymes, growth factors, peptides, polypeptides, antibodies, other nitrogenous natural molecules, combinations thereof, and the like. Other natural components may include derivatives of the foregoing, for example modified hyaluronic acid, dextran, other polysaccharide, polymers and/or polypeptides, including aminated polysaccharides which may be naturally derived, synthetic, or biologically derived. As previously mentioned, the nucleophilic component may also comprise a synthetic polymer which may have a synthetic water soluble or non-water soluble core, having nucleophilic functional groups.

In one particular embodiment, the nucleophilic component comprises albumin and the electrophilic component comprises a multi-arm PEG functionalized with multiple NHS groups. In embodiments the components may be in solution(s) which may be combined to permit formation of a hydrogel.

In embodiments, the albumin may be placed in solution utilizing a suitable solvent. Such as, for example buffers such as sodium carbonate, sodium borate, sodium phosphate, Hanks Balanced Salt Solution. Dulbecco's Modified Eagle's Medium, water, saline and the like. The solvents utilized herein have a pH of from about 5 to about 9. The nucleophilic component may be present in a solution including the aforementioned solvent(s) at a concentration from about 0.01 grams/milliliter (g/mL) to about 1 g/mL, in embodiments from about 0.1 g/mL to about 0.5 g/mL.

Similarly, the electrophilic component, such as a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic component, may be present in a solution including the above buffer(s) at a concentration from about 0.01 g/mL to about 1 g/mL, in embodiments from about 0.1 g/mL to about 0.5 g/mL. In certain embodiments, the electrophilic component may be provided neat, that is, the molecular weight is of a certain range that the electrophilic component is in liquid form and does not need to be mixed with a buffer. For example, a multi-arm PEG functionalized with electrophilic groups having a molecular weight of less than or equal to 2500D may be provided neat.

Once the electrophilic and nucleophilic components mix, they crosslink to create a hydrogel. The hydrogel comprises a ratio of the nucleophilic component to the electrophilic component, in embodiments, albumin to the multi-arm PEG of from about 0.1:1 to about 100:1, and in certain embodiments, from about 0.5:2.

The crosslinked hydrogel may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing the two components that are physically separated until physically combined, or as a consequence of a prevalent condition in the physiological environment, including: temperature, pH, ionic strength, combinations thereof, and the like. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like. In some embodiments, the buttress may include a biocompatible multi-component system that spontaneously crosslinks when the components are mixed.

In embodiments, one or more components having biodegradable linkages present in between functional groups may be included to make the lyophilized buttress biodegradable. These linkages may be, for example, esters, which may be hydrolytically degraded in physiological solution. The use of such linkages is in contrast to protein linkages that may be degraded by proteolytic action. A biodegradable linkage optionally also may form part of a water soluble core of one or more of the components. Alternatively, or in addition, functional groups of components may be chosen such that the product of the reaction between them results in a biodegradable linkage. For each approach, biodegradable linkages may be chosen such that the resulting biodegradable crosslinked buttress degrades or is absorbed in a desired period of time. Generally, biodegradable linkages may be selected that degrade the buttress under physiological conditions into non-toxic or low toxicity products.

Buttresses of the present disclosure may degrade due to hydrolysis or enzymatic degradation of the biodegradable region. The degradation of buttresses containing any synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a buttress with a desired degradation profile, from a few days to months, using a proper degradable segment.

When the electrophilic component and nucleophilic component are admixed, they create a hydrogel. As used herein, the term "hydrogel" refers to the gel created when the nucleophilic and electrophilic components are mixed and crosslinked. The hydrogel may then be applied to the stapling instrument, and more specifically to the staple jaws including the staple cartridge and/or staple anvil. As the hydrogel is applied to the staple jaws, the hydrogel can flow into the staple pockets and staple forming buckets, and once lyophilized, portions of the buttress disposed in the staple pockets and staple forming buckets mechanically fixate or secure the buttress to the staple jaws. In alternate embodiments, the hydrogel may additionally only be applied to the cartridge surface and may flow into the staple pockets. Alternatively, the hydrogel may be applied to the anvil surface and may flow into the staple forming buckets. The hydrogel may be directly applied to the staple jaws utilizing methods including spraying, brushing, and extruding. In one particular embodiment, the hydrogel is applied to the staple jaws utilizing an air assisted sprayer. As will be later described, the hydrogel is subsequently lyophilized, creating the tissue buttress. The lyophilized buttress is later implanted in situ.

In other embodiments, the electrophilic and nucleophilic components may be separately applied to the staple jaws. For example, the first component (e.g., the nucleophilic component) may be applied to a surface of the cartridge, creating a first layer. Next, the second component (e.g., the electrophilic component) may be applied over the first layer, enabling the two components to mix and subsequently crosslink to create a hydrogel on the cartridge surface. Similar to above, the first and second components or alternatively, the hydrogel, can flow into the staple pockets. Alternatively, or in addition to, the first or second components and/or the hydrogel may be applied to the anvil surface.

Once the hydrogel has been created, the hydrogel is subsequently lyophilized to create the tissue buttress. The terms "lyophilization," "lyophilize," and "lyophilized," as used herein includes a freeze-drying process in which a material is subject to temperatures at which the given material may freeze, and lower pressure, which drives the frozen water in a material to sublimate directly from the solid phase to the gas phase. In embodiments, the disposable loading unit having the hydrogel disposed thereon may be placed in a lyophilization chamber. Alternatively, the staple jaw(s), e.g., the anvil and cartridge, which contain the hydrogel, may be placed in a lyophilization chamber. Lyophilization parameters are within one skilled in the art. Portions of the buttress disposed within the staple pockets or staple forming buckets anchor the buttress to the staple jaws and in particular, to the cartridge or anvil. In embodiments, at least a portion of the buttress is mechanically retained within the staple pockets and/or staple forming buckets, providing temporary fixation of the buttress to the stapling instrument.

In certain embodiments, the buttress may be created prior to attachment to the staple jaws. For example, the electrophilic and nucleophilic components may be contacted or mixed and allowed to crosslink in a mold of desired dimensions. Next, the mold may be placed in a lyophilization chamber, converting the hydrogel to a foam buttress. The buttress is subsequently attached to "the staple jaw(s) for implantation in situ.

Figure 4A:
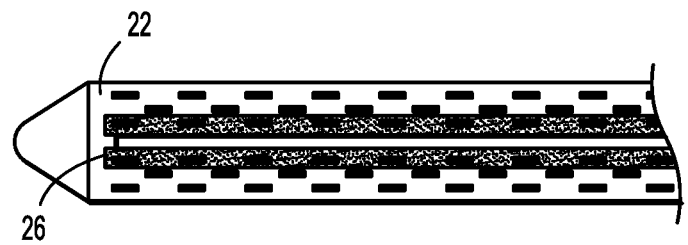
FIGS. 4A-4C are various embodiments of a staple buttress in accordance with the present disclosure.
Figure 4B:
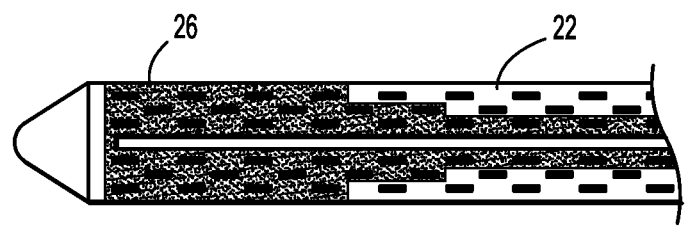
Figure 4C:
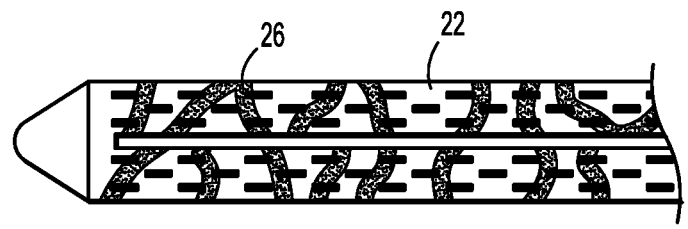

The buttress may be secured to the entire staple jaw(s) or a portion thereof. The buttress may be disposed on one or both of the staple jaws, e.g., anvil and cartridge. Alternatively, the buttress may solely be present on the innermost row of staple pockets (FIG. 4A), providing maximum tissue support and hemostasis at the stapled tissue edge. Alternatively, the buttress may be discontinuous across the cartridge surface, for example, the buttress being disposed on every other staple pocket. In another example, the buttress may be disposed on the surface of the cartridge utilizing a specific (FIG. 4B) or random pattern (FIG. 4C). It should be understood that although the above embodiments are illustrated on the staple cartridge surface, the buttress may additionally, or alternatively, be disposed on the staple anvil surface.

The thickness of the buttress may vary across the surface of the staple jaws. For example, the buttress may be thicker towards the stapled tissue edge, providing more tissue compression and hemostasis. Methods for varying buttress thickness include, but are not limited to applying thicker layers of the hydrogel, or alternatively, the electrophilic and nucleophilic components for increased compression. Once lyophilized, corresponding portions of the buttress may be thicker and thinner. For example, a thicker buttress may be disposed towards the center, or knife slot, of the stapling instrument. In alternate embodiments, the buttress may be thicker towards the proximal end of the loading unit and thinner towards the distal end of the loading unit.

It should be noted that the composition of the buttress may vary along the jaws of the surgical instrument. For example, a more absorbent buttress may be present closest to the cut edge, and a less absorbent buttress may be present further from the cut edge. As tissue bleeds more at the cut edge of tissue it may be more important to have a composition which can absorb more fluids closer to the site of injury (cut edge). This may be achieved by varying the hydrogel composition or the ratio of the electrophilic component to the nucleophilic component along the staple cartridge and/or anvil.

Further, the composition or crosslinking of the buttress may be tailored to control the water absorption of the buttress. For example, a highly swellable buttress composition may be disposed adjacent to the innermost row of staples, while a lower swelling buttress composition may be disposed adjacent to the outermost row of staples. A buttress which is highly swellable may be more beneficial closer to the cut edge of tissue as the highly swellable buttress may absorb more fluids or may better support the tissue. This may be achieved by tailoring the nucleophilic and electrophilic compositions. Alternatively, the crosslinking of the polymer buttress may vary along surface of the stapling jaws. For example, a buttress having a highly crosslinked polymer network may swell less compared to a buttress with fewer crosslinks. The lesser crosslinked buttress may be disposed closer to the cut edge of the cartridge, enabling the buttress to swell and absorb more fluids and provide enhanced tissue compression compared to a more crosslinked, lower swelling buttress. For example, an electrophilic crosslinker such as a 4-arm NHS PEG may swell more compared to an 8-arm NHS PEG.

In embodiments, the buttress is porous, having openings or pores over at least a portion of a surface thereof. The pores may be in sufficient number and size so as to interconnect across the entire thickness of the porous layer, creating an open pore structure. In other embodiments, the pores do not interconnect across the entire thickness of the porous layer, creating a closed pore structure. In yet other embodiments, the pores do not extend across the entire thickness of the porous layer, but rather are present at a portion of the surface thereof. Those skilled in the art reading the present disclosure will envision other pore distribution patterns and configurations for the porous layer.

The pores may be formed using any method suitable to forming a foam or sponge including, but not limited to the lyophilization or freeze-drying of the hydrogel composition. Porous buttress materials can be at least 0.2 cm thick, in embodiments from about 0.3 to about 1.5 cm thick. Porous buttress materials can have a density of no more than about 75 mg/cm$^2$ and, in embodiments below about 20 mg/cm$^2$. The size of the pores may be from about 20 µm to about 300 µm, in embodiments from about 100 µm to about 200 µm.

Additionally, the buttress may further include a non-porous layer. The non-porous layer may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like. The non-porous layer may be combined with the foam layer utilizing methods including but not limited to adhesives, glues, and solvent welding.

The buttress may further include a reinforcement member for providing increased strength or support. The reinforcement member may be positioned within or on a surface of the buttress. Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped fiber may be from 0.1 mm to 100 mm in length, in embodiments, 0.4 mm to 50 mm in length.

In some embodiments, at least one bioactive agent may be combined with the buttress. The bioactive agent may be incorporated into tissue buttress, for example, by incorporation into at least one of the electrophilic component, nucleophilic component, hydrogel or the foam buttress. In these embodiments, the buttress serves as a vehicle for delivery of the bioactive agent. The term "bioactive agent", as used herein, in its broadest sense includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly(vinyl pyrrolidone), carboxymethyl cellulose, hyaluronic acid, polyethylene oxide, polyvinyl alcohols and combinations thereof.

Suitable antimicrobial agents which may be included as a bioactive agent of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent of the present disclosure.

Other bioactive agents which may be included in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included herein include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Embodiments of the presently disclosed buttress and methods for attachment to surgical instruments will now be described in detail with reference to the drawings wherein like numerals designate identical or corresponding elements in each of the several views. As is common in the art, the term 'proximal" refers to that part or component closer to the user or operator, i.e., surgeon or physician, while the term "distal" refers to that part or component further away from the user.

Referring now to FIG. 1, a linear surgical stapling instrument or surgical stapler 10 is disclosed for use in stapling tissue and applying layers of the buttress material between the staples and underlying tissue. Surgical stapler 10 generally includes a handle 12 having an elongate tubular member 14 extending distally from handle 12. A jaw assembly 16 is mounted on a distal end 18 of elongate tubular member 14. Jaw assembly 16 includes a first jaw, including a staple forming anvil 20 and a second jaw, including a staple containing cartridge or staple cartridge 22. Staple cartridge 22 may be permanently affixed to elongate tubular member 14 or may be detachable and thus replaceable with a new staple cartridge 22. Staple clinching anvil 20 is movably mounted on distal end 18 of elongate tubular member 14 and is movable between an open position, spaced apart from staple cartridge 22 to a closed position, substantially adjacent staple cartridge 22.

Surgical stapler 10 includes a trigger 32 movably mounted on handle 12. Actuation of trigger 32 initially operates to move anvil 20 from the open to the closed position relative to staple cartridge 22 and subsequently actuate surgical stapler 10 to apply lines of staples to tissue. A rotation knob 34 is provided on handle 12 to properly orient jaw assembly 16 relative to the tissue to be stapled. Rotation of rotation knob 34 relative to handle 12 rotates elongate tubular member 14 and jaw assembly 16 relative to handle 12 so as to properly orient jaw assembly 16 relative to the tissue to be stapled.

Referring to FIG. 2, a driver 36 is provided to move anvil 20 between the open and closed positions relative to staple cartridge 22. Driver 36 moves through a longitudinal slot 38 formed in anvil 20. A knife blade (not shown) is associated with driver 36 to cut tissue captured between anvil 20 and staple cartridge 22 as driver 36 passes through slot 38.

Staple cartridge 22 further includes a buttress 26 disposed thereon. The buttress 26 is releasably affixed to staple cartridge 22. A portion of the buttress 26 may be at least partially disposed within at least one staple pocket, securing the buttress to the staple cartridge 22. In certain embodiments, the buttress 26 is positioned within a plurality of staple pockets 92, providing temporary fixation of the buttress to the cartridge. Additionally, the buttress 26 may frictionally engage the staple legs 134 and 136, and in some embodiments, the staple backspan 132. The buttress 26 is at least partially positioned on an inwardly facing surface of at least staple cartridge 22 in order to facilitate passage of surgical stapler 10 into the body of a patient without risk of tearing or wrinkling of the respective buttress as surgical stapler 10 is inserted into and manipulated within the body of a patient.

Optionally, the anvil 20 may include a buttress 24 which may be retained on the surface of the anvil through frictional engagement between the buttress 24 and the staple forming bucket 48. As previously described, upon lyophilization, the buttress expands and frictionally engages the sidewalls of the staple forming bucket 48, securing the buttress to the anvil surface. In further embodiments, an adhesive may be provided to secure the buttress to the anvil surface. In yet alternate embodiments, additional mechanical fixation means may be provided to secure the buttress to the staple jaw(s). Suitable examples of which are described in U.S. Patent Publication No. 2011010170, assigned to Tyco Healthcare Group LP, d/b/a, Covidien, the contents of which are incorporated by reference herein. Other methods for attaching the buttress to a staple cartridge or anvil include but are not limited to U.S. Patent Publication Nos. 2010/0116868; 2010/0147922, 2011/0036895; and 2011/0101070, each of which are assigned to Tyco Healthcare Group LP d/b/a Covidien, the entire contents of which are incorporated by reference herein.

Figure 5:
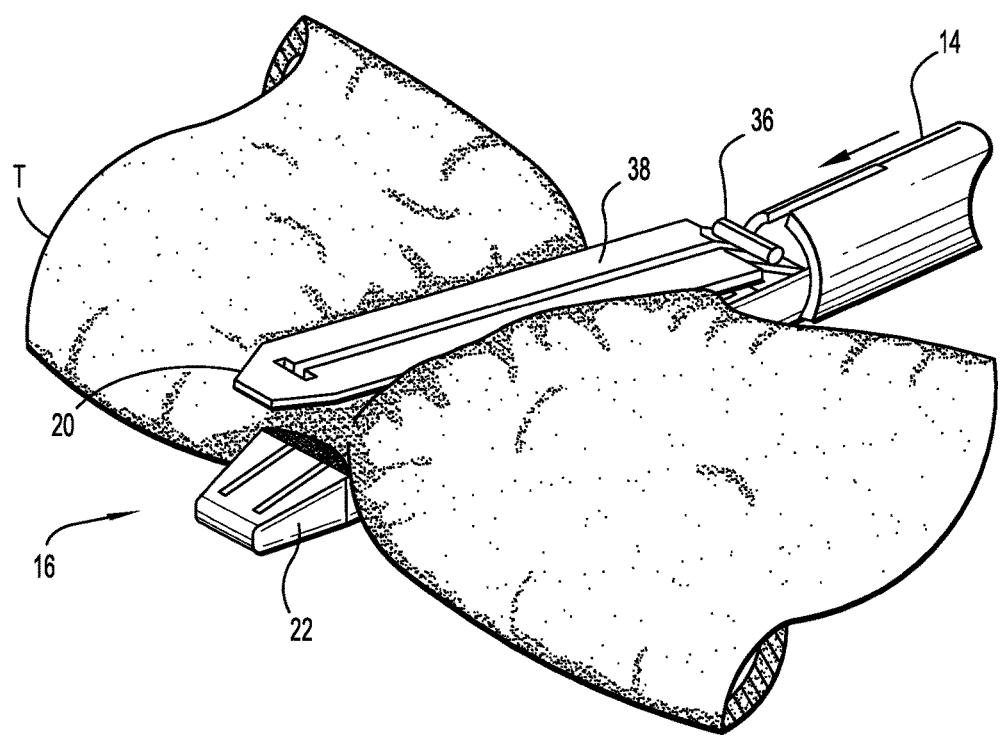
FIG. 5 is a perspective view of the distal end of the surgical stapling instrument of FIG. 1 in position on tubular tissue.
Figure 6:
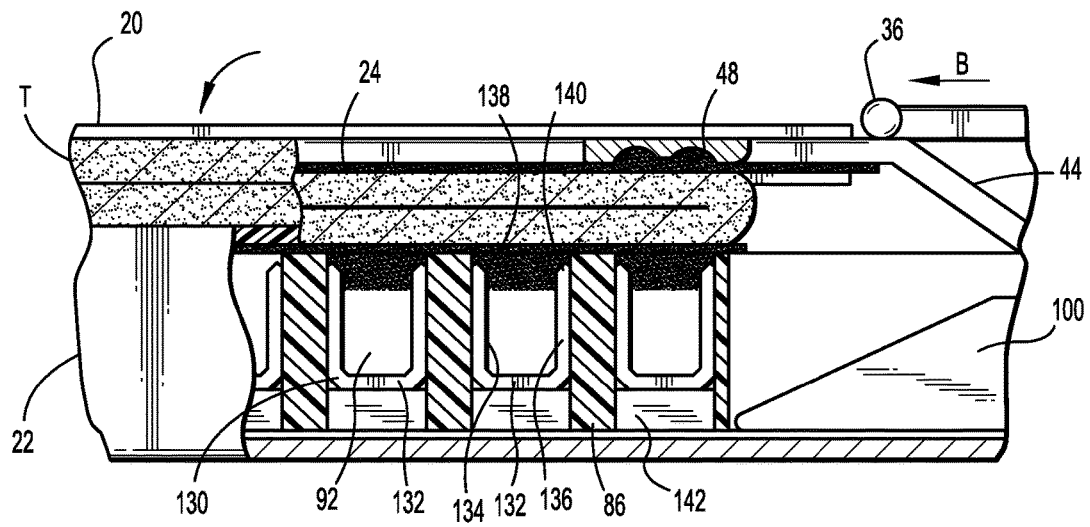
FIG. 6 is a cross-sectional view of a tissue section captured between an anvil and staple cartridge of the surgical instrument of FIG. 1.

Referring now to FIGS. 5 through 9, and initially with respect to FIGS. 5 and 6, the use of surgical stapler 10 to staple and divide a tubular tissue section T will now be described. Initially, jaw assembly 16, including anvil 20 and staple containing cartridge 22 are positioned around the tissue T to be stapled. Driver 36 is in a proximal position relative to slot 38. As best shown in FIG. 6, staple containing insert 86 includes staples 130 positioned within staple pockets 92. Staples 130 are of a conventional type and include a backspan 132 having a pair of legs 134 and 136 extending from backspan 132. Legs 134 and 136 terminate in tissue penetrating tips 138 and 140. Pushers 142 are located within staple pockets 92 and are positioned between staples 132 and the path of drive bar 100.

Figure 7:
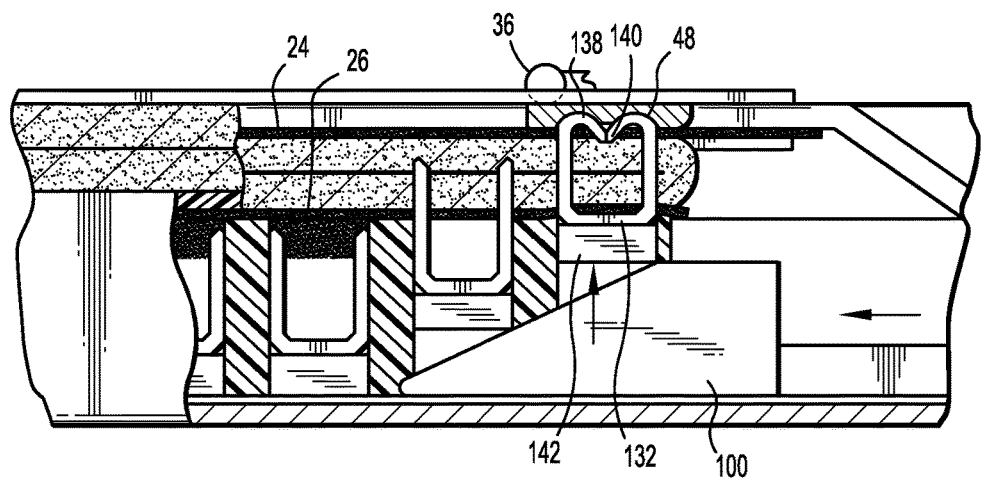
FIG. 7 is a cross-sectional view showing initial actuation of the surgical stapling instrument of FIG. 1.

Referring now to FIG. 6, surgical stapler 10 is initially actuated by movement of trigger 32 relative to handle 12 (FIG. 1) causing driver 36 to move in the direction of arrow B thereby causing anvil 20 moved to the closed position relative to staple cartridge 22. As best shown in FIG. 7, as drive bar 100 advances distally, drive bar 100 urges pushers 142 upwardly against backspans 132 of staples 130, driving staples 130 through first buttress 26, into tissue T, through second buttress 24 and towards staple forming buckets 48 in anvil 20. Tissue penetrating tips 138 and 140 are bent within staple forming buckets 48, and backspan 132 secures buttress material 26 against tissue T.

Figure 8:
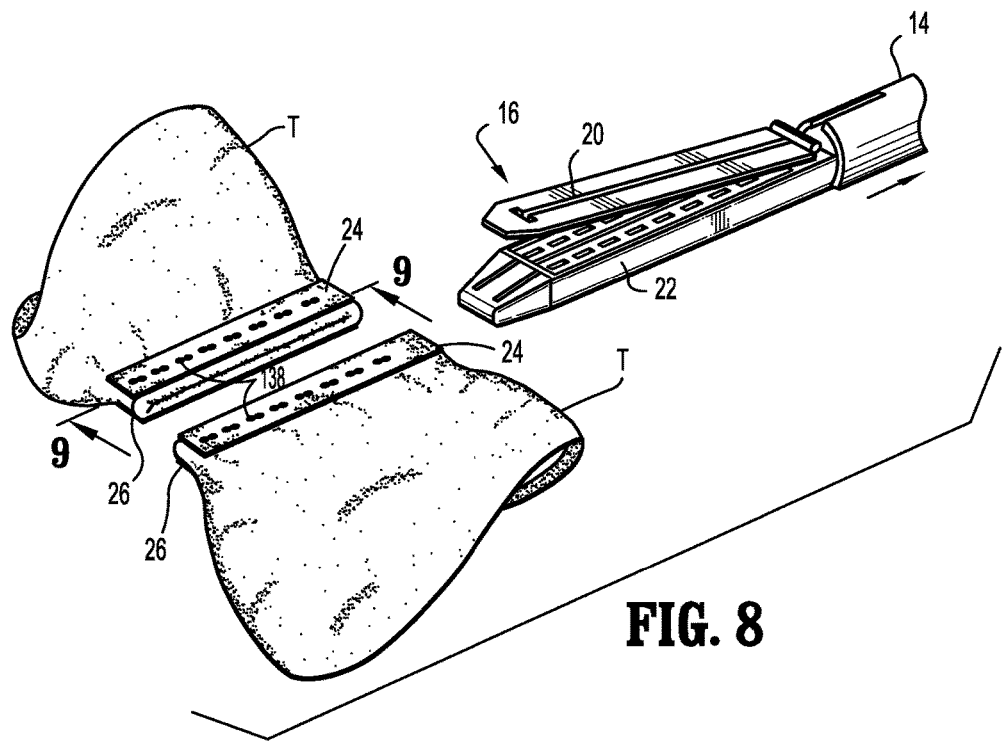
FIG. 8 is a perspective view of the distal end of the surgical stapling instrument and stapled tissue sections.

While not specifically shown, upon full actuation of surgical stapler 10, a knife blade associated with surgical stapler 10 and carried by driver 36 cuts tissue T, as well as anvil buttress material 24 and cartridge buttress material 26 between the rows of now formed staples 132. As shown in FIG. 8, in one embodiment, upon movement of anvil 20 to the open position, spaced apart from staple cartridge 22, anvil buttress material 24 pulls away from anvil 20 as described hereinabove.

Figure 9:
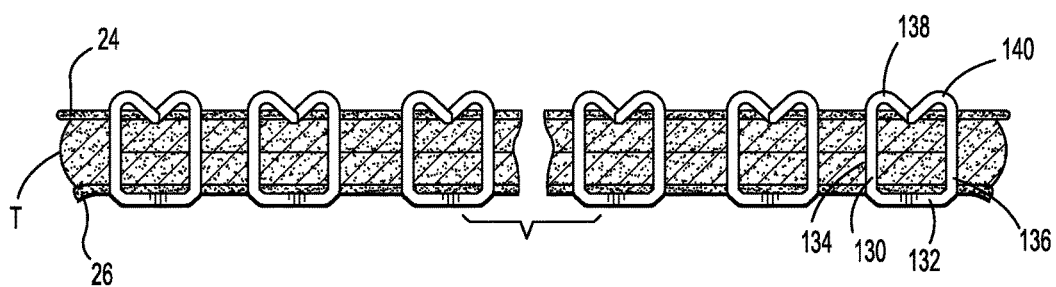
FIG. 9 is a cross-sectional view of the stapled tissue section taken along line 14-14 of FIG. 8.

The resulting tissue T stapled closed with staples 130 is best illustrated in FIG. 9. Specifically, cartridge buttress 26 is secured against tissue T by backspans 132 of staples 130 and anvil buttress 24 is secured against tissue T by the now formed tissue penetrating tips 138 and 140 of staples 130. In this manner, anvil buttress 24 and cartridge buttress 26 are stapled to tissue T thereby sealing and/or reinforcing staple lines created by staples 130.

Figure 10:
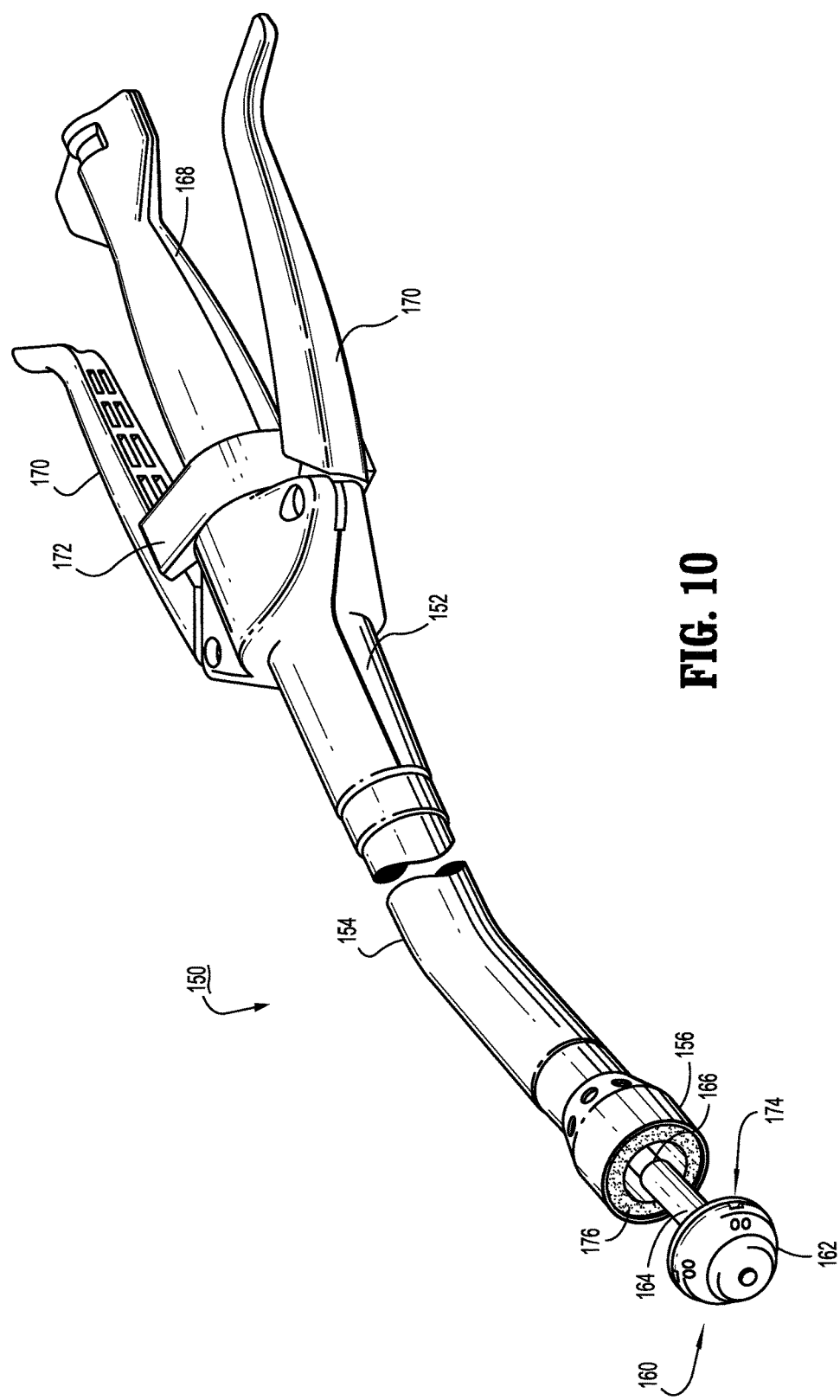
FIG. 10 is a perspective view of a circular stapling instrument including a buttress in accordance with a one embodiment of the present disclosure.

Referring now to FIGS. 10-17, and initially with respect to FIG. 10, buttress materials attached to a circular surgical stapler will now be described. Circular surgical stapler 150 is of known type generally including a handle 152 having an elongate member 154 extending distally from handle 152. A staple containing head or cartridge 156 is provided on a distal end of elongate member 154. Staple containing cartridge 156 houses staples (not shown) for insertion through tissue. Specifically, circular surgical stapler 150 is configured to apply one or more circular rows of staples to staple together two tubular tissue sections. An anvil 160 is provided to form the staples into a closed shape about tissue. Anvil 160 includes an anvil cap 162 having an anvil shaft 164 extending proximally from anvil cap 162. A shaft 166 extends from elongate member of 154 and is configured to releasably engage anvil shaft 164. An approximator 168 is rotatably mounted on handle 152 and is provided to approximate or move anvil 160 toward and away from staple containing cartridge 156.

A pair of arms 170 are pivotally mounted on handle 152 and are provided to actuate circular surgical stapler 150 so as to eject staples out of staple containing cartridge 156. A lock 172 is provided on handle 152 to block and prevent actuation of circular surgical stapler 150 prior to anvil 160 being approximated adjacent staple containing cartridge 156. Circular surgical stapler 150 is provided with an anvil buttress material 174 releasably affixed to anvil cap 162 and a cartridge buttress material 176 provided on staple containing cartridge 156. Anvil buttress 174 and cartridge buttress 176 serve to reinforce and/or seal a staple line applied to tubular tissue sections by circular surgical stapler 150.

Figure 11:
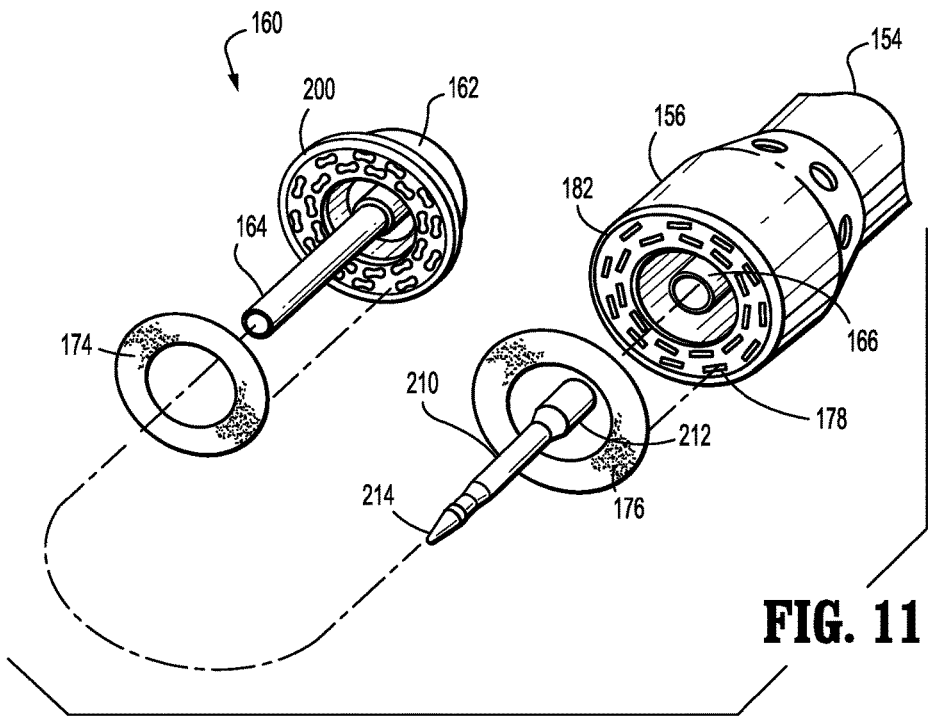
FIG. 11 is a perspective view, with parts separated, of the distal end of the circular surgical stapling instrument of FIG. 10.

Referring now to FIG. 11, staple containing cartridge 156 includes a plurality of staple pockets 178 containing staples as discussed in more detail below. Similar to that discussed hereinabove with respect to staple containing cartridge 22 of surgical stapler 10, the buttress 174, 176 is provided on both the anvil and cartridge tissue-facing surface and as shown herein. A portion of the buttress 174 and 176 is disposed within the staple pockets and the staple forming buckets, securing the buttress 174, 176 to the staple jaws.

As shown, in one embodiment, in order to secure anvil 160 to stapler 150, there is provided an adapter 210. A proximal end 212 of adapter 210 is configured to engage shaft 166 of circular surgical stapler 150. Adapter 210 includes a pointed distal end 214 configured to pierce tissue sections as well as engage anvil shaft 164.

Figure 12:
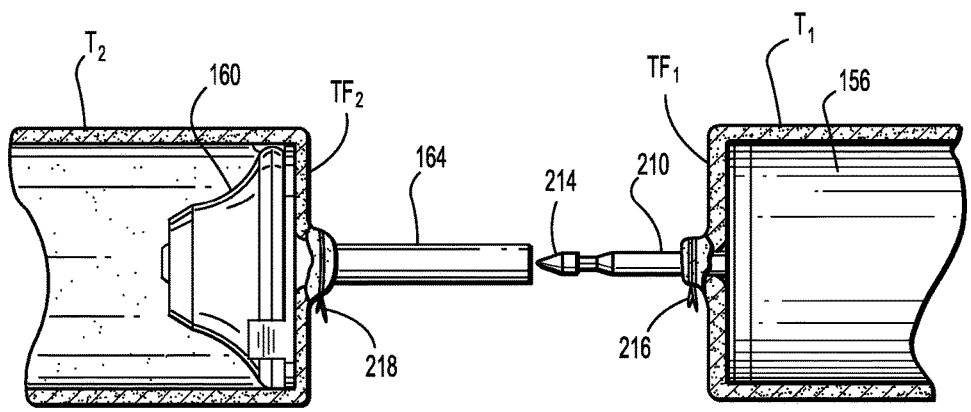
FIG. 12 is a side view, partially shown in section, of the distal end of the circular surgical stapling instrument of FIG. 10 positioned in a tubular tissue section.
Figure 13:
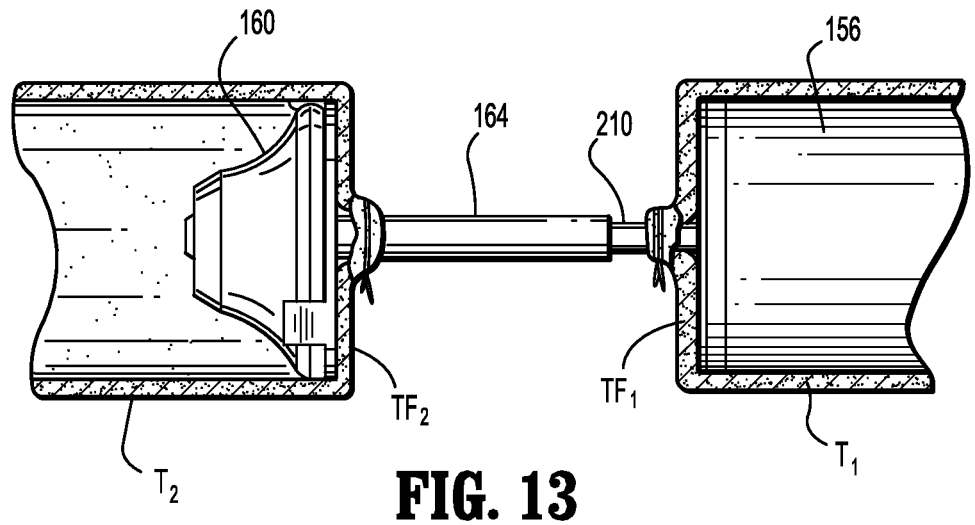
FIG. 13 is a side view illustrating the anvil of the circular surgical stapling instrument attached to the stapling containing head of the circular surgical stapling instrument.
Figure 14:
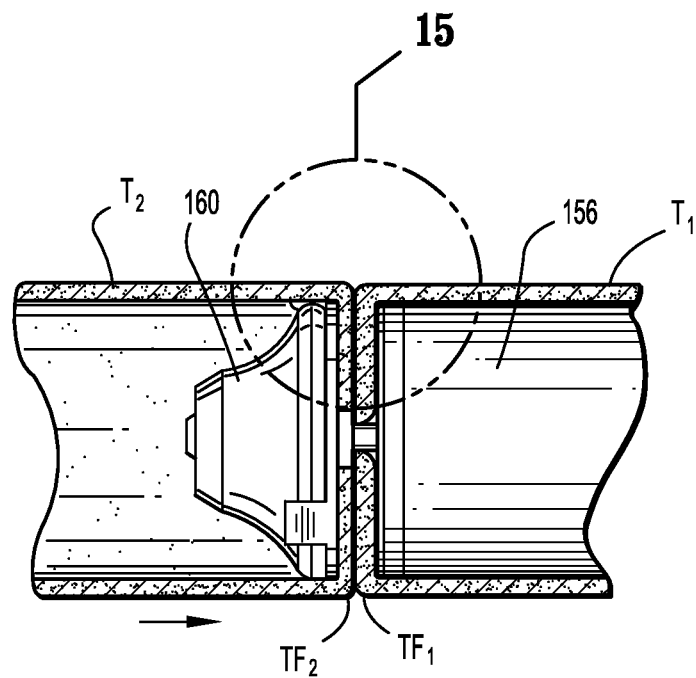
FIG. 14 is a side view showing the anvil and staple containing head approximated.

Referring now to FIGS. 10 and 12 to 17, and initially with regard to FIG. 12, the use of circular surgical stapler 150 to connect two tubular tissue sections and apply buttress material will now be described. Initially, staple containing cartridge 156 is positioned within a first tubular tissue section $T_1$ such that adapter 210 extends beyond tissue $T_1$. A purse string suture 216 is formed about tissue $T_1$ and adapter 210 to form an inwardly directed tissue face $TF_1$. Likewise, anvil 160 is positioned within a second tubular tissue section $T_2$ such that anvil shaft 164 projects beyond tissue section $T_2$ and is secured thereto by a second purse string suture 218 forming a second inwardly directed tissue face $TF_2$. Adapter 210 is then inserted within anvil shaft 164 to connect staple containing cartridge 156 to anvil 160 (FIG. 13).

Once staple containing cartridge 156 has been connected to anvil 160, approximator 168 on handle 152 is rotated to draw anvil 160 toward staple containing cartridge 156 and thus bring first tissue face $TF_1$ into flush engagement with the second tissue face $TF_2$ and in a position to be stapled. (See FIG. 14)

Figure 15:
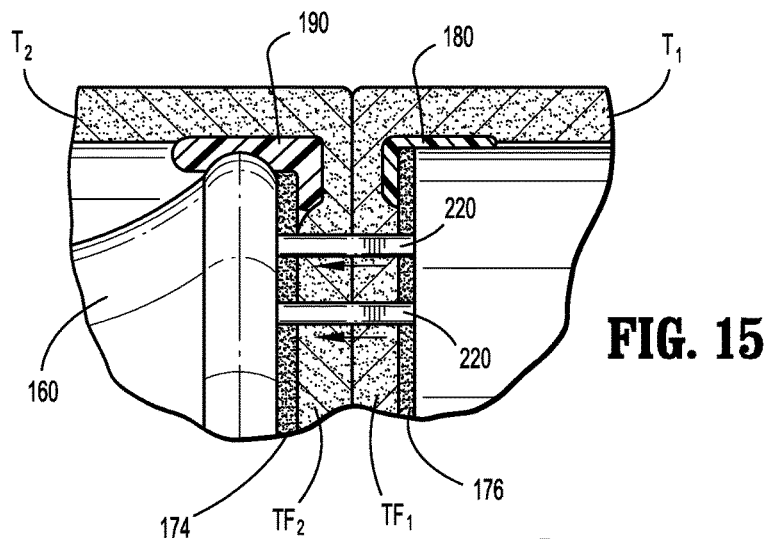
FIG. 15 is an enlarged area of detail view of FIG. 14.
Figure 16:
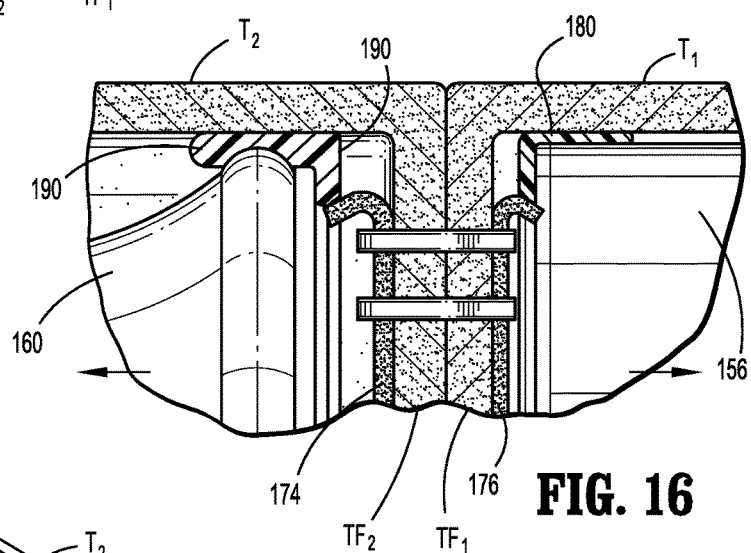
FIG. 16 is a detail view showing actuation of the circular surgical stapling instrument.

Referring to FIGS. 15 and 16, and as discussed hereinabove, staple containing cartridge 176 includes a plurality of staples 220. Circular surgical stapler 150 is actuated by releasing lock 172 and pivoting arms 170 (FIG. 15) thereby ejecting staples 220 out of staple containing cartridge 156 and through the tissue sections. Specifically, staples 220 pass through first tissue face $TF_1$, cartridge buttress 176, second tissue face $TF_2$ and anvil buttress 174. Staples 20 are clinched closed about anvil buttress material 174 by staple forming buckets 186 (FIG. 11).

Figure 17:
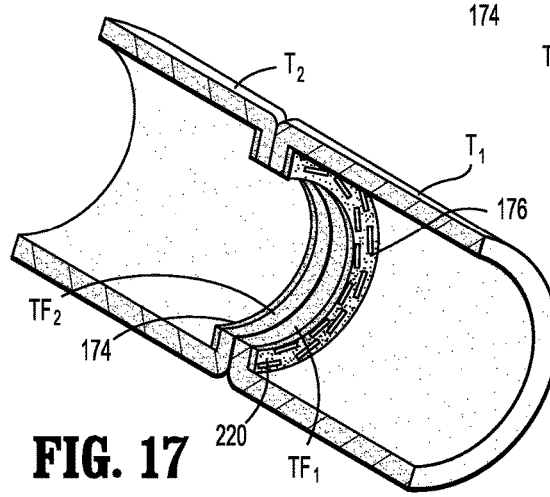
FIG. 17 is a perspective view, partially shown in section, of the stapled tubular tissue sections.

The resultant stapled tissue sections are clearly illustrated in FIG. 17. Once the tissue sections have been stapled, a circular knife (not shown) associated with circular surgical stapler 150 may be used to core out portions of the stapled tissue sections.

It should be noted that the disclosed buttress and process for making therein enable the buttress to be positioned on the surgical stapler at the time of manufacture eliminates the need for installation in the operating room. Additionally, since the buttress materials are generally localized on the faces of the anvil and staple cartridge, the surgical stapler can be easily inserted through an access device without interference from the buttress material.

It will be understood that various modifications may be made to the embodiments disclosed herein. For example, the disclosed buttress material retainer systems may be incorporated in open or endoscopic surgical stapling instruments. Further, a limited amount of adhesive may be used to temporarily secure the buttress material to the anvil or staple containing cartridge. Therefore, the above description should not be construed as limiting, but merely as exemplifications of particular embodiments. Those skilled in the art will envision other modifications within the scope and spirit of the claims appended hereto.

What is claimed is:

1. A method of making a tissue buttress comprising the steps of:
    applying a hydrogel comprising an electrophilic component and a nucleophilic component to at least one of a first jaw and a second jaw of a surgical stapler,
    allowing the electrophilic component and the nucleophilic component to react to form the hydrogel; and
    lyophilizing the hydrogel disposed on at least one of the first jaw and the second jaw of the surgical stapler to form a tissue buttress.

2. The method of claim 1, wherein lyophilizing the hydrogel at least temporarily secures the buttress to at least one of the first jaw and the second jaw.

3. The method of claim 1, wherein at least one of the first jaw and the second jaw define staple pockets for retaining staples.

4. The method of claim 3, wherein a portion of the buttress is at least partially disposed within at least one staple pocket.

5. The method of claim 1, wherein the electrophilic component comprises N-hydroxysuccinimide.

6. The method of claim 1, wherein the nucleophilic component comprises a natural component.

7. The method of claim 1, wherein the nucleophilic component comprises albumin having a molecular weight of from about 60,000 g/mol to about 70,000 g/mol.

8. The method of claim 1, wherein the electrophilic component further comprises polyethylene glycol.

9. The method of claim 1, wherein the electrophilic component comprises multiple arms.

10. The method of claim 1, wherein the electrophilic component is applied to one of the first jaw and the second jaw and the nucleophilic component is applied to the other of the first jaw and the second jaw.

11. A method of making a tissue buttress comprising the steps of:
applying a polymer composition comprising an electrophilic component and a nucleophilic component to at least one of a staple anvil and a staple cartridge;
allowing the electrophilic component and the nucleophilic component to react to form the polymer composition disposed on at least one of the staple anvil and staple cartridge; and,
lyophilizing the polymer composition to create a tissue buttress.

12. The method of claim 11, wherein lyophilizing the polymer composition at least temporarily secures the buttress to at least one of the staple anvil and staple cartridge.

13. The method of claim 11, wherein the electrophilic component comprises N-hydroxysuccinimide.

14. The method of claim 11, wherein the nucleophilic component comprises a natural component.

15. The method of claim 11, wherein the nucleophilic component comprises albumin having a molecular weight of from about 60,000 g/mol to about 70,000 g/mol.

16. The method of claim 11, wherein the electrophilic component further comprises polyethylene glycol.

17. The method of claim 11, wherein the electrophilic component comprises multiple arms.

18. The method of claim 11, wherein the electrophilic component is applied to at least one of the staple anvil and the staple cartridge and the nucleophilic component is applied to the other of the staple anvil and the staple cartridge.

19. The method of claim 1, wherein the tissue buttress provides hemostasis in situ.

20. The method of claim 11, wherein the tissue buttress provides hemostasis in situ.

* * * * *